United States Patent [19]

Barry, III et al.

[11] Patent Number: 5,610,198
[45] Date of Patent: Mar. 11, 1997

[54] ANTI-MYCOBACTERIAL COMPOSITIONS AND THEIR USE FOR THE TREATMENT OF TUBERCULOSIS AND RELATED DISEASES

[75] Inventors: Clifton E. Barry, III, Hamilton; Ying Yuan, Missoula, both of Mont.

[73] Assignee: The United States of America as represented by the Department of Health and Human Services, Washington, D.C.

[21] Appl. No.: 210,519

[22] Filed: Mar. 18, 1994

[51] Int. Cl.$^6$ .................................................. A61K 31/10
[52] U.S. Cl. .................... 514/712; 568/39; 568/41
[58] Field of Search ................ 554/85; 574/712; 568/39, 41

[56] References Cited

U.S. PATENT DOCUMENTS 4,444,766  4/1984  Bosies et al. ........................ 424/211
4,739,105  4/1988  Courtney, Jr. et al. .

FOREIGN PATENT DOCUMENTS 0401193    12/1990   European Pat. Off. .
2508904    11/1981   France .
3423691C1  12/1985   Germany .
WO93/03005  2/1993   Japan .

*Primary Examiner*—Elli Peselev
*Attorney, Agent, or Firm*—Townsend and Townsend and Crew

[57] ABSTRACT

Compounds, pharmaceutical compositions, and methods for the treatment of mycobacterial diseases, such as tuberculosis and leprosy, are provided. Use of the compounds for promoting an antiseptic condition of a surface are also included. Some of the preferred compounds include thiatetracosanoic acids, esters, and fluorinated analogs.

5 Claims, 3 Drawing Sheets

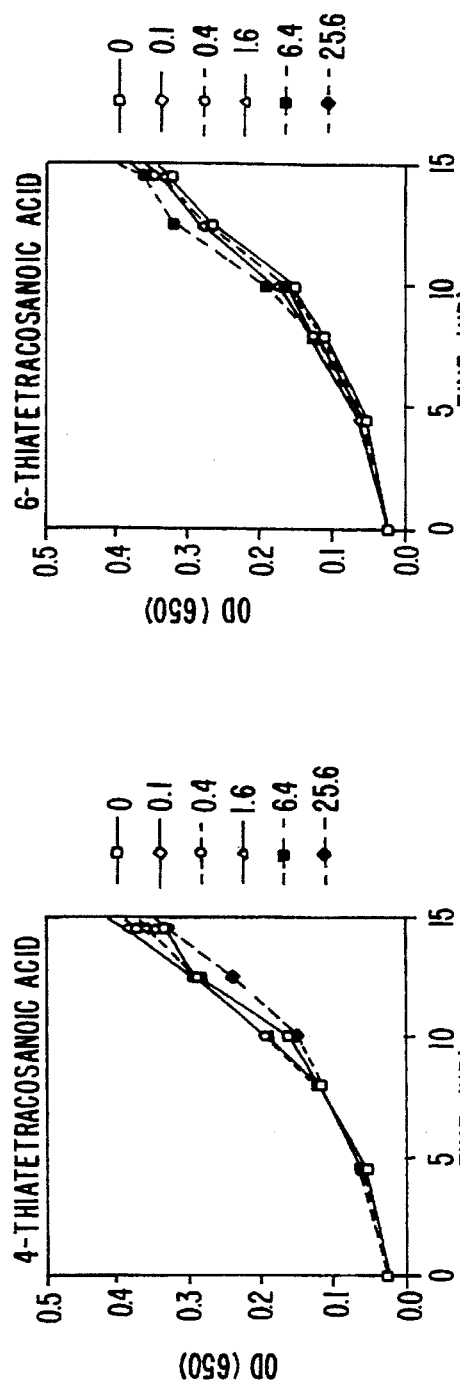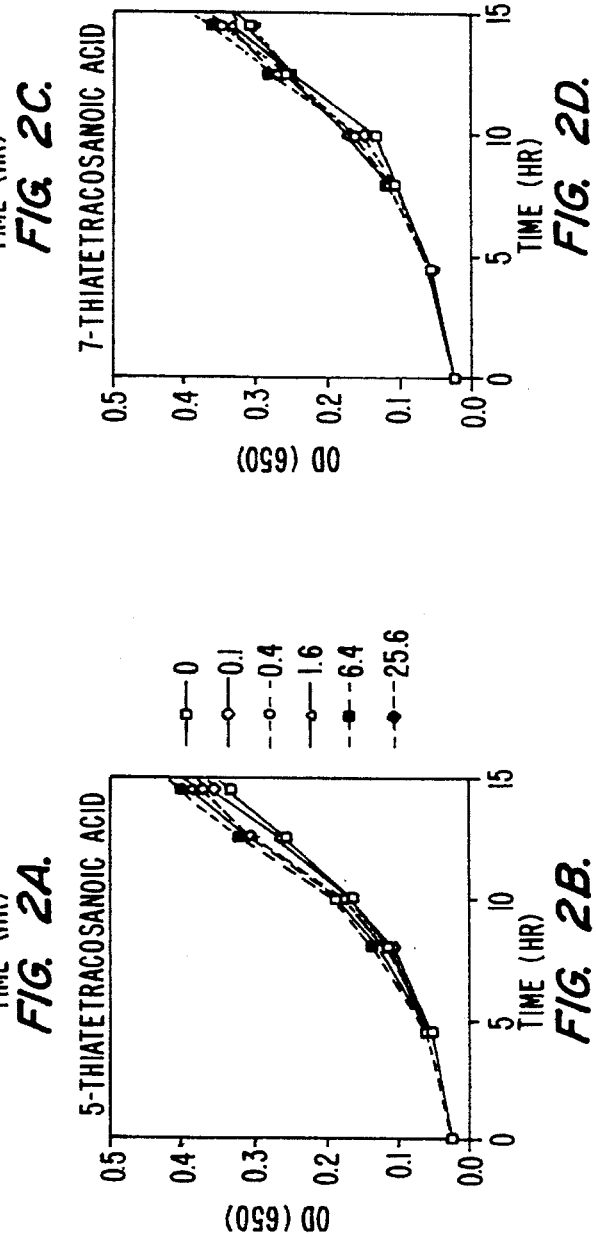

ANTI-MYCOBACTERIAL COMPOSITIONS AND THEIR USE FOR THE TREATMENT OF TUBERCULOSIS AND RELATED DISEASES

BACKGROUND OF THE INVENTION

Mycobacterium is a genus of bacteria which are aerobic, mostly slow growing, slightly curved or straight rods, sometimes branching and filamentous, and distinguished by acid-fast staining. They are sometimes referred to as acid-fast bacilli (AFB) as application of alcohol (e.g., acid-alcohol or 95% ethanol with 3% hydrochloric acid) will not decolorize bacilli stained with basic dye. Typically, the mycobacteria are obligate aerobes, and they can be characterized as gram-positive. However, some have stated that gram-staining is unhelpful or unclassifiable. The genus mycobacterium includes the highly pathogenic organisms that cause tuberculosis (*M. tuberculosis* and sometimes *M. bovis*) and leprosy (*M. leprae*). There are many other species of mycobacterium, some of which are important in veterinary medicine.

The following species of the genus mycobacterium are known pathogens for humans, and some are pathogenic for certain animals as well: *M. tuberculosis, M. leprae, M. avium-intracellulare, M. bovis, M. chelonei* (also known as borstelense and abscessus), *M. africanum, M. marinium* (also known as balnei and platypoecilus, the causative agent of "swimming pool granuloma"), *M. buruli* (also known as ulcerans), *M. fortuitum* (also known as giae, minetti, and ranae), *M. haemophilum, M. intracellulare, M. kansasii* (also known as luciflavum), *M. littorale* (also known as xenopi), *M. malmoense, M. marianum* (also known as scrofulaceum and paraffinicum), *M. simiae, M. szulgai, and M. ulcerans* (which is the agent responsible for Buruli ulcer).

Mycobacterium which are pathogenic for animals but not believed to be pathogenic for humans include the following: *M. avium* (also known as brunense), *M. flavascens, M. lepraemurium, M. microti, and M. paratuberculosis* (which is the causative agent for Johne's Disease). The following species of the genus mycobacterium are believed to be non-pathogenic: *M. gordonae* (also known as aquae), *M. gastri, M. phlei* (also known as moelleri and as timothy bacillus), *M. nonchromogenicum, M. smegmatis, M. terrae, M. triviale,* and *M. vaccae*.

Additionally, certain mycobacteria other than *M. tuberculosis* and *M. bovis* are alternatively known as non-tuberculosis mycobacteria. They are divided into four groups, also known as Runyon groups, based on pigmentation and growth rate. Each group includes several species. Group I refers to slow-growing photochromogens; Group II refers to slow-growing scotochromogens; Group III refers to slow-growing nonphotochromogens; and Group IV refers to rapidly-growing mycobacteria. The non-tuberculosis mycobacteria are also called atypical or anonymous mycobacteria.

Tuberculosis (TB) is an acute or chronic infection caused by *M. tuberculosis* and occasionally by *M. bovis*. Tuberculosis continues to be a major health concern in both the United States and abroad, exacting a yearly mortality of 3 million lives. See Styblo, et al., *Bull. Int. Union Tuberc.* 56:118–125 (1981). Of special concern is the increased risk to HIV-positive persons who are either exposed to the tubercle bacilli for the first time or are subject to reinfection/reactivation of dormant lesions. See, Styblo, *Rev. Inf. Dis.* 11:Suppl. 2, S339–S346 (1989). In addition, the appearance of multiply drug-resistant strains of *Mycobacterium tuberculosis* is urban areas in developed countries places many new populations at risk. See, Snider, et al., *N. Eng. J. Med.* 326:703–705 (1992). According to the World Health Organization's estimates, 1.7 billion people (one-third of the world population) are infected with the tubercle bacilli. Sixty million people are currently afflicted with active *Mycobacterium tuberculosis*, another 10 million cases arise annually and more than 3 millions die each year. See, Kaufman, et al., *Trends in Microbiology* 1:2–5 (1993). This means that tuberculosis is responsible for 6% of the total global mortality and more than 25% of all preventable deaths. In 1992, about 26,000 cases of active TB were reported in the United States, an 18% increase since 1988. Similar increases have been observed in many European countries; 33% in Switzerland, 30% in Denmark, 20% in Norway, 18% in Ireland, 17% in Austria, 9% in The Netherlands, 5% in Sweden and 4% in the United Kingdom. See, Kaufman, ibid. There are also a significant number of AIDS patients who become infected with TB. It has been estimated that worldwide there are 4.4 million people co-infected with HIV and tuberculosis and in some African states, 40% of tuberculosis patients are HIV-positive.

Although commonly thought of as a pulmonary infection, TB is well known to afflict many parts of the body. In addition to pulmonary TB, examples of other foci of tubercular infection include miliary TB (generalized hematogenous or lymphohematogenous TB), central nervous system TB, pleural TB, TB pericarditis, genitourinary TB, TB of the gastrointestinal tract, TB peritonitis, TB of the adrenals, TB of the liver, TB of the bones and joints (for example, TB spondylitis or Pott's Disease), TB lymphadenitis, and TB of the mouth, middle ear, larynx, and bronchial tree.

Tuberculosis has been characterized as a life-long balance between the host and the infecting organism. Pulmonary or extrapulmonary foci may reactivate at any time, often after long periods of latency. Prevention of TB has been attempted by vaccination with BCG, which is an attenuated strain of *M. tuberculosis*.

Chemoprophylaxis of TB is practiced in appropriate cases and generally consists of isoniazid. Usually, chemoprophylaxis is recommended in selected individuals who are tuberculin-positive (by a skin test, discussed below) without overt disease. Examples include very young adults and children, recent tuberculin converters, individuals with pulmonary infiltrates of unknown ideology, people receiving prolonged corticosteroid therapy, postgastrectomy patients with roentgen evidence of inactive pulmonary TB, and all patients with silicosis. Occasionally, treatment of tuberculin-negative individuals is appropriate. Examples include an infant suffering a brief exposure to a known infection and persons having reduced immune responsiveness.

Some of the signs and symptoms of pulmonary TB are cough, sputum production, hemoptysis, pain in the chest wall or pleural pain, dyspnea, and, in the case of extrapulmonary TB, signs and symptoms related to the infected foci. Frequently, a patient remains asymptomatic for prolonged periods of time.

Definitive diagnosis by cultural identification of the causative agent is preferred. The tuberculin test is an adjunct to diagnosis. A standard tuberculin test is performed with purified protein derivative (PPD) administered intradermally (the Mantoux test). Various modifications include Pirequet's (scratch) test, multiple-puncture tine and Heaf tests. Because the diagnosis of TB can be elusive, particularly in its extrapulmonary forms, tissue biopsy may be indicated to obtain a sample for acid-fast staining and culture studies.

Conventional therapy for TB includes treatment with isoniazid, ethambutol, streptomycin, rifampin, rifabutin, clarithromycin, ciprofloxacin, clofazamine, azithromycin, ethionamide, amikacin and resorcinomycin A. In rare cases, isoniazid may be used alone. However, the usual initial treatment for pulmonary tuberculosis includes isoniazid in combination with at least one other drug, such as ethambutol, streptomycin, rifampin or ethionamide. Retreatment of pulmonary tuberculosis typically involves drug combinations including rifampin and other drugs as noted above. Development of resistance of the causative agent to anti-TB drugs, especially isoniazid, is well known. Extrapulmonary tuberculosis is also usually treated with a combination including rifampin and at least one of the other three drugs mentioned.

The anti-TB antibiotic isoniazid (isonicotinic acid hydrazide) is frequently effective, but isoniazid often causes severe, sometimes fatal, hepatitis. The risk of hepatitis increases with the patient's age. Additionally, isoniazid causes peripheral neuropathy in some recipients in a dose-related fashion. Rifampin, another antibiotic used to treat TB, must be used in conjunction with another drug such as isoniazid. This requirement for combination therapy with rifampin applies to the initial treatment as well as the retreatment of pulmonary TB.

Usually, isoniazid, rifampin, ethambutol and ethionamide are given orally. Streptomycin is typically given intramuscularly. Amikacin is given intramuscularly or intravenously. Clofazimine, which is also used to treat leprosy, is given orally.

Amikacin is a semisynthetic aminoglycoside antibiotic derived from Kanamycin A. For its preparation see U.S. Pat. No. 3,781,268. For a review see Kerridge, *Pharmacological and Biochemical Properties of Drug Substances* 1:125–153, M. E. Goldberg, ed. (1977). Amikacin is usually administered intramuscularly or intravenously. For additional information including clinical pharmacology, indications, side effects and dosages, see the *Physicians Desk Reference*, 42 ed. (1988) at pages 744–746 (hereinafter, PDR).

Clofazimine is an antibacterial agent also known as LAMPRENE®. For its preparation, see Barry, et at., *Nature* 179:1013 (1957). For a review see Karat, et at., *Brit. Med. J.* 3:175 (1971). Clofazimine is generally given orally. For additional information including clinical pharmacology, precautions and dosages, see the *PDR* at page 982.

Ethionamide is an antibacterial agent also known as AMIDAZINE® and TRECATOR®. See British Patent No. 800,250. This drug is typically given orally. For further information including precautions and dosages, see the *PDR* at page 2310.

Ciprofloxacin is a broad spectrum synthetic antibacterial agent for oral usage. It is also known as CIPRO®. It is typically given in total daily dosages of 500 to 1,000 milligrams which is usually given in 2 equal doses in 24 hours. For further information see the *PDR* (1989) at pages 1441–1443.

Leprosy or Hansen's Disease is a chronic infectious disease caused by *M. leprae*. Leprosy is conveniently divided into four types, namely indeterminate leprosy, tuberculoid leprosy, lepromatous leprosy, and dimorphous (borderline) leprosy. In any of its forms, leprosy is characterized by invasion of the peripheral nerves by the causative agent. Usually, a lack of sensation or anesthesia is produced in the relevant skin area. Paralysis and deformity follow sensory loss. Diagnosis is typically established by biopsy. Conventional treatment includes administration of dapsone (4,4'-diaminodiphenyl sulfone, DDS). Dapsone is typically given orally for prolonged periods, such as for two years after diagnosis. For certain forms of leprosy, such as the dimorphous and lepromatous forms, combination therapy with rifampin and/or dapsone is administered. Sometimes the drug clofazimine is given alone or in combination with dapsone. Dapsone alone is the conventional therapy for indeterminate and tuberculoid types of leprosy.

Because of some of the difficulties and inadequacies of conventional therapy for TB and other mycobacterial infections, new therapeutic modalities are desirable.

SUMMARY OF THE INVENTION

We have discovered that compounds of formula I are effective at inhibiting the growth of pathogenic mycobacteria.

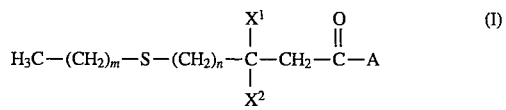

As a result, the present invention provides pharmaceutical compositions containing compounds of formula I wherein n, m, $X^1$, $X^2$, and A are as described below. The present invention further provides methods for the treatment of mycobacterial infection in animals as well as a method for promoting an antiseptic condition on a surface using the compounds described. The pharmaceutical compositions and methods of the present invention may also contain other antimycobacterial agents such as isoniazid, ethambutol, dapsone, amikacin, ethionamide and rifampin.

BRIEF DESCRIPTION OF THE DRAWINGS

FIG. 1A shows treatment of the cell culture with 4-thiatetracosanoic acid.

FIG. 2A, B, C, D shows growth curves of *M. smegmatis* mc²155 treated with various concentrations of each of four different thiatetracosanoic acid analogs. The ordinate graphs time in minutes and the coordinate graphs the optical density at 650 nm. The various concentrations of the analogs are 0, 0.1, 0.4, 1.6, 6.4 and 25.6 µg/mL.

FIG. 2A shows treatment of the cell culture with 4-thiatetracosanoic acid. FIG. 2B shows treatment of the cell culture with 5-thiatetracosanoic acid. FIG. 2C shows treatment of the cell culture with 6-thiatetracosanoic acid. FIG. 2D shows treatment of the cell culture with 7-thiatetracosanoic acid.

DETAILED DESCRIPTION

Definitions

Figure 1A:
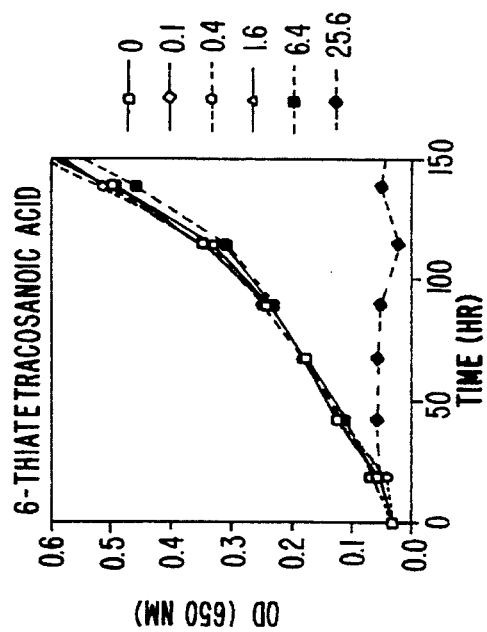
FIGS. 1A, B, C, and D shows growth curves of *M. tuberculosis* H37Ra treated with various concentrations of each of four different thiatetracosanoate analogs. The ordinate graphs time in hours and the coordinate graphs the optical density at 650 nm. The various concentrations of the analogs are 0, 0.1, 0.4, 1.6, 6.4 and 25.6 µg/mL.
Figure 1C:
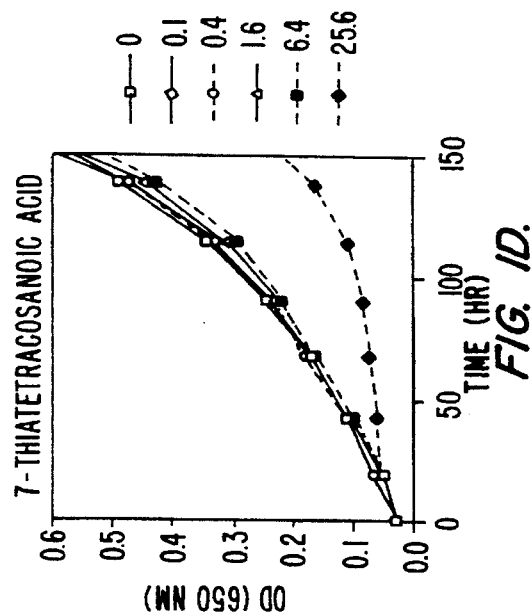
FIG. 1C shows treatment of the cell culture with 6-thiatetracosanoic acid.
Figure 1B:
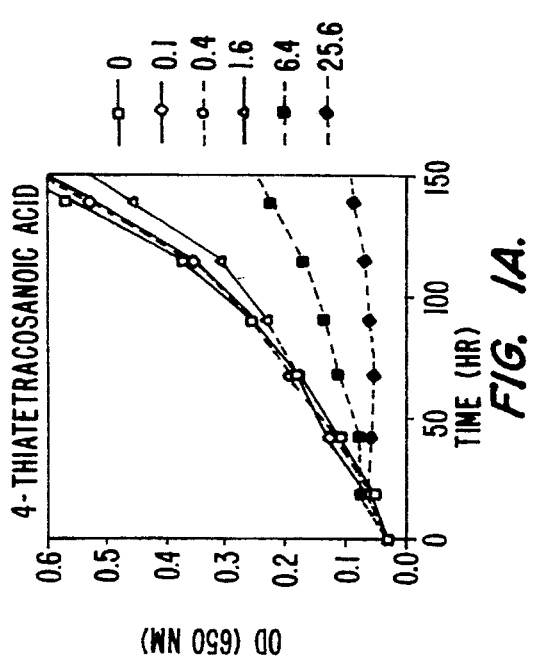
FIG. 1B shows treatment of the cell culture with 5-thiatetracosanoic acid.
Figure 1D:
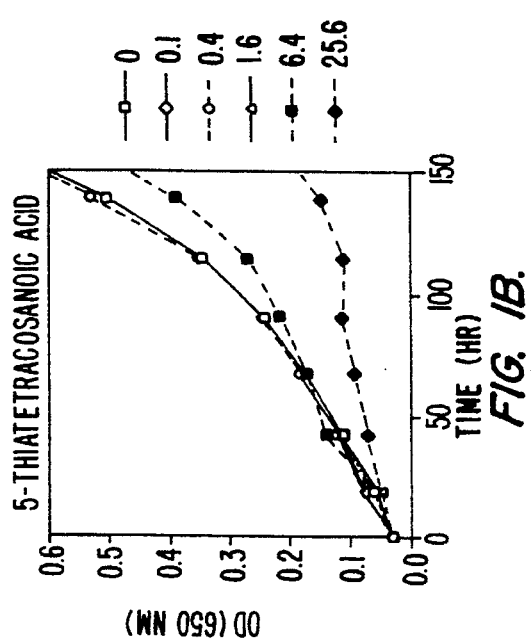
FIG. 1D shows treatment of the cell culture with 7-thiatetracosanoic acid.

The terms "treatment", "therapy" and the like refer to improvement in the recipient's status. The improvement can be subjective or objective and related to features such as symptoms or signs of the disease or condition being treated. For example, if the patient notes decreased coughing, less sputum production, better endurance or an improved sense of well being, then successful treatment has occurred. Similarly, if the clinician notes objective improvement on a test, such as improvement of the chest to auscultation or percussion, better pulmonary function test (PFT) results, decreased evidence of infection or an improved chest roentgen (X-ray), then treatment has also been successful. Prevention of deterioration of the recipient's status is also included by the term. For instance, a therapeutic composition can be given to individuals who are at high risk for or in very early stages of development of TB or other mycobacterial infection to prevent progression of the infection. An example of such a patient is one who has a normal chest roentgen but a newly positive tuberculin test, such as a Mantoux skin test.

The term "ameliorate" or "amelioration" includes any of the arrest, prevention, decrease, and improvement in any of the symptoms, signs, and features of mycobacterial infection, both temporary and long term. Amelioration of mycobacterial infection is a further example of successful treatment or therapy.

"Material," "sample" and "tissue" in the context of the invention refer to animal tissue, cells or portions thereof which can include, for example, whole cells, parts of cells and extracellular material and lysates of cells, or parts of cells and extracellular material. The term "cell" refers to animal, plant, and micro-organism cells. The term "tissue" embraces extracellular material and acellular material of animal origin. For example, a tissue sample can be obtained by biopsy, and cellular fluid samples can be aspirated or removed from a patient. Any such sample can be tested, for instance, by staining, histologic techniques, cultures, or biochemical studies.

In one aspect, the invention provides pharmaceutical compositions which contain compounds of formula I in a pharmaceutically acceptable carrier.

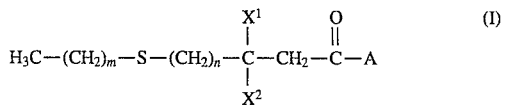

(I)

The symbol n represents an integer of from 0 to 3.

The symbol m represents an integer of from 12 to 23, such that the sum of n+m is from 15 to 23.

The group A represents —OH, —OR or —O$^-$ along with any pharmaceutically acceptable salts. In instances in which A is —OR, R is an alkyl group having from 1 to 10 carbon atoms, preferably from 1 to 4 carbon atoms.

The symbols $X^1$ and $X^2$ may be the same or different and are either H or F.

In certain preferred embodiments, the pharmaceutical composition contains a compound of formula I in which n is an integer of from 0 to 3 and m is an integer of from 15 to 20 such that n+m is from 18 to 20.

In further preferred embodiments, the pharmaceutical compositions contain a compound of formula I in which n is an integer of from 0 to 3, m is an integer of from 15 to 20 such that n+m is from 18 to 20, most preferably 19, R is an alkyl group having from 1 to 4 carbon atoms, and $X^1$ and $X^2$ are both H.

In still further preferred embodiments, the pharmaceutical compositions contain a compound of formula I wherein n is an integer of from 0 to 3, m is an integer of from 16 to 19 such that n+m is 19, $X^1$ and $X^2$ are both H, and A is —O$^-$ along with its pharmaceutically acceptable salts.

In other preferred embodiments, the compositions of the present invention contain a compound of formula I along with one or more of the following: isoniazid, ethambutol, streptomycin, rifampin, dapsone, rifabutin, clarithromycin, ciprofloxacin, clofazamine, azithromycin, ethionamide, amikacin or resorcinomycin A.

The compounds used in the present invention are either commercially available or may be prepared using conventional techniques. General synthetic routes to the compounds tested are provided below. Particular conditions are known to those of skill in the art. See, March, *Advanced Organic Chemistry. Reactions, Mechanisms and Structures*, Fourth Ed., John Wiley & Sons, New York, N.Y. (1992) and Fieser, et al., *Reagents for Organic Synthesis* volumes 1–16, John Wiley & Sons, New York, N.Y. (1992) both of which are incorporated herein by reference. Table A illustrates compounds which are useful in the present invention.

TABLE A $$H_3C-(CH_2)_m-S-(CH_2)_n-\underset{X^2}{\underset{|}{\overset{X^1}{\overset{|}{C}}}}-CH_2-\overset{O}{\overset{\|}{C}}-A$$

| Compound Number | n | m | $X^1$ | $X^2$ | A |
|---|---|---|---|---|---|
| 1 | 0 | 19 | H | H | OH |
| 2 | 1 | 18 | H | H | OH |
| 3 | 2 | 17 | H | H | OH |
| 4 | 3 | 16 | H | H | OH |
| 5 | 3 | 16 | H | H | $OCH_3$ |
| 6 | 3 | 16 | H | H | $OC_2H_5$ |
| 7 | 1 | 17 | F | F | OH |
| 8 | 1 | 17 | F | F | $OC_2H_5$ |

Compounds 1 to 4 correspond to 4-thiatetracosanoic acid, 5-thiatetracosanoic acid, 6-thiatetracosanoic acid and 7-thiatetracosanoic acid, respectively. Synthetic strategies to produce these compounds typically involve one of two routes. In the first route, a mercapto-substituted alkanoic acid such as 3-mercaptopropanoic acid is alkylated with a long-chain alkyl bromide such as 1-bromoeicosane to produce the desired alkylthioalkanoic acid. These acids can be converted to esters (for example 5 and 6) by techniques well known in the art, for example, by treatment with diazomethane to produce a methyl ester or by treatment with an alcohol (i.e., methanol, ethanol, butanol or octanol) in the presence of an acid (HCl or $H_2SO_4$).

A second route to the alkylthioalkanoic acids of formula I is by treatment of a long-chain alkyl thiol, such as heptadecanethiol, with a suitable bromoalkanoic acid, such as 5-bromopentanoic acid or 6-bromohexanoic acid. Alkylthioalkanoic acids produced by this method can also be esterified as described above. Fluorinated alkylthioalkanoic acids and esters (compounds 7 and 8) can be synthesized by treatment of a β-keto alkylthioalkanoic ester with such reagents as diethylaminosulfur trifluoride (DAST) or $SF_4$. For example, treatment of ethyl 4-chloroacetoacetate with 1-octadecanethiol provides ethyl 3-oxo-4-octadecylthiobutanoate, which can be converted to compound 8 by treatment with either $SF_4$ or DAST. Treatment of 8 with KOH in ethanol provides the corresponding acid 7. Other compounds used in the present invention can be similarly prepared.

The pharmaceutically acceptable salts are obtained in the usual manner. Examples include neutralization of compounds of general formula I with non-toxic inorganic or organic bases such as ammonia, sodium hydroxide, potassium hydroxide, lithium hydroxide, morpholine, trimethylamine, and piperidine. Additionally, salts may be exchanged using techniques such as ion-exchange chromatography.

In another aspect, the present invention provides a method for treating a mycobacterial infection in an animal which harbors the infection. In this method, the animal is treated with an effective amount of a compound of formula I.

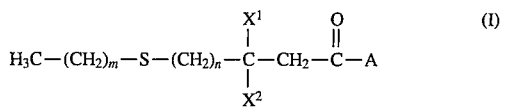

The symbol n represents an integer of from 0 to 3.

The symbol m represents an integer of from 12 to 23, such that the sum of n+m is from 15 to 23.

The group A represents —OH, —OR or —O$^-$ along with any pharmaceutically acceptable salts. In instances in which A is —OR, R is an alkyl group having from 1 to 10 carbon atoms, preferably from 1 to 4 carbon atoms.

The symbols $X^1$ and $X^2$ may be the same or different and are either H or F.

In certain preferred embodiments, the method of administrating the compound is by oral, inhalation, or intravenous administration. The effective amount of the compound is in the range of from about 0.01 mg/kg to about 100 mg/kg of body weight of the animal. In specific preferred embodiments, the animal to be treated is a human, a cow, a sheep or a goat.

In still other preferred embodiments, the infection to be treated is caused by any of *M. tuberculosis*, *M. leprae*, *M. bovis*, and *M. intracellulare*. Specifically, the infection can be evidenced by a positive tuberculin test, chest X-ray findings, staining (such as acid-fast staining) or culture-positivity for mycobacteria.

In yet another preferred embodiment, the infection is treated with a combination including a compound of formula I and an anti-mycobacterial agent. Preferably, the anti-mycobacterial agent is one or more of the following: isoniazid, ethambutol, streptomycin, rifampin, dapsone, rifabutin, clarithromycin, ciprofloxacin, clofazamine, azithromycin, ethionamide, amikacin or resorcinomycin A.

In still another aspect, the present invention provides a method for promoting an antiseptic condition on a surface, by applying a compound of formula I to the surface. In preferred embodiments, the method of application is by spraying, pouring, wiping or immersing the surface.

Formulations

Means of preparation, formulation and administration are known to those of skill. See generally *Remington's Pharmaceutical Sciences* 17th ed., Mack Publishing Co., Easton, Pa. (1985), *Remington's* hereinafter.

Using a method of the invention, compounds are typically administered to human patients parenterally, topically or enterally in solid or liquid form. Preferably, the compositions are administered in unit dosage forms suitable for single administration of precise dosage amounts. The compositions may also include, depending on the formulation desired, pharmaceutically-acceptable, non-toxic carriers or diluents which are vehicles commonly used to form pharmaceutical compositions for animal or human administration.

Additionally, the compositions of the present invention may be administered encapsulated in liposomes, pharmaceutical delivery vehicles wherein the active ingredient is contained either dispersed or variously present in corpuscles consisting of aqueous concentric layers adherent to lipidic layers. The active ingredient, depending upon its solubility, may be present both in the aqueous layer and in the lipidic layer, or in what is generally termed a liposomic suspension. The hydrophobic layer, generally but not exclusively, comprises phospholipids such as lecithin and sphingomycelin, steroids such as cholesterol, more or less ionic surfactants such as dicetylphosphate, stearylamine, or phosphatidic acid, and/or other materials of a hydrophobic nature. The diameters of the liposomes generally range from about 15 nm to about 5 microns.

An aqueous injection medium is preferred. The diluent is selected so as not to affect the biological activity of the combination. Examples of such diluents are water, the various saline solutions, Ringer's solution, dextrose solution, and Hank's solution. In addition, the pharmaceutical composition or formulation may also include additives such as other carriers; adjuvants; or nontoxic, nontherapeutic, nonimmunogenic stabilizers solubilizing agents; buffers and the like. Effective amounts of such diluent or additive are those amounts which are effective to obtain a pharmaceutically acceptable formulation in terms of solubility, biological activity, etc.

Additives include, for example, tartrate and citrate buffers, ethanol, complex formers (such as ethylenediaminetetraacetic acid and the non-toxic salts thereof) and high molecular weight polymers (such as liquid polyethylene oxide) for viscosity regulation. Liquid carder materials for injection solutions are sterile and are preferably placed into ampules. Solid carder materials include, for example, starch, lactose, mannitol, methylcellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and/or sweetening agents.

Preparations of the therapeutic compound either for systemic or local delivery may be employed and may contain excipients as described above for parenteral administration and other excipients used in a topical preparation such as cosolvents, surfactants, oils, humectants, emollients, preservatives, stabilizers and antioxidants. Any pharmacologically acceptable buffer may be used, e.g., tris or phosphate buffers.

Liposomes for use with the invention are formed from standard vesicle-forming lipids, which generally include neutral and negatively charged phospholipids and a sterol, such as cholesterol. The selection of lipids is generally guided by consideration of, e.g., liposome size and stability of the liposomes in the bloodstream.

Typically, the major lipid component in the liposomes is phosphatidylcholine. Phosphatidylcholines having a variety of acyl chain groups of varying chain length and degree of saturation are available or may be isolated or synthesized by well-known techniques. In general, less saturated phosphatidylcholines are more easily sized, particularly when the liposomes must be sized below about 0.3 microns, for purposes of filter sterilization. Phosphatidylcholines containing saturated fatty acids with carbon chain lengths in the range of $C_{14}$ to $C_{22}$ are preferred. Phosphatidylcholines with mono or diunsaturated fatty acids and mixtures of saturated and unsaturated fatty acids may also be used.

Other suitable lipids include phosphonolipids in which the fatty acids are linked to glycerol via ether linkages rather than ester linkages. Liposomes useful in the present invention may also be composed of sphingomyelin or phospholipids with head groups other than choline, such as ethanolamine, serine, glycerol and inositol.

A variety of methods are available for preparing liposomes as described in, e.g., Szoka et al., *Ann. Rev. Biophys. Bioeng.* 9:467 (1980), U.S. Pat. Nos. 4,235,871, 4,501,728, 4,837,028, the text *Liposomes*, Marc J. Ostro, ed., Chapter 1, Marcel Dekker, Inc., New York (1983), and Hope, et al., *Chem. Phys. Lip.* 40:89 (1986), all of which are incorporated herein by reference.

To get sufficient quantities of a therapeutic compound delivered to the correct in vivo site, a more lipid-soluble derivative can be useful. For example, the methyl esters, ethyl esters and other alkyl esters of formula I could be used. In addition, if these compounds are degraded in vivo, it can be advantageous to make derivatives which are more stable to β-oxidation, such as the appropriate fluorinated derivatives. Fluorination at the carbon position beta to the carbonyl is known to slow the process of β-oxidation. Accordingly, preferred compositions of the present invention contain compounds of formula I wherein one or both of the hydrogens attached to the β-carbon are replaced by fluorine (i.e., $X^1$ and/or $X^2$ are F).

The therapeutic compound is also administered by aerosol to achieve localized delivery to the lungs (inhalation therapy), as well as for application to mucous membranes and to the skin. See, for example, *Remington 's*, Chapter 93, pages 1662–1670. This formulation involves preparing an aqueous aerosol, liposomal preparation or solid particles containing compounds of the invention or derivatives thereof. A nonaqueous (e.g., fluorocarbon propellent) suspension could be used. Sonic nebulizers preferably are used in preparing aerosols. Sonic nebulizers minimize exposing the therapeutic compound to shear, which can result in degradation of the compound.

Ordinarily, an aqueous aerosol is made by formulating an aqueous solution or suspension of the therapeutic compound together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. The formulations are sterile. Aerosols generally are prepared from isotonic solutions.

In preparing formulations using compounds of the invention, the practitioner is advised that Tween 80 interferes with drug uptake and efficacy, probably by interfering with transport. See Example 6 and FIG. 3. Thus, although Tween 80 could be used in a therapeutic formulation, the dosage should be adjusted upward appropriately.

Alternatively, the therapeutic compound is formulated into topical preparations for local therapy by including a therapeutically effective concentration of the therapeutic compound in a dermatological vehicle. The amount of the therapeutic compound to be administered, and the compound's concentration in the topical formulations, depends upon the vehicle selected, the clinical condition of the patient, the side effects and the stability of the compound in the formulation. Thus, the physician will employ the appropriate preparation containing the appropriate concentration of the therapeutic compound in the formulation, as well as the amount of formulation administered, depending upon clinical experience with the patient in question or with similar patients.

The concentration of the therapeutic compound for topical formulations is in the range of about 0.01 mg/mL to about 1.0 mg/mL. Solid dispersions of the therapeutic compound as well as solubilized preparations can be used. Thus, the precise concentration to be used in the vehicle will be subject to modest experimental manipulation in order to optimize the therapeutic response. Greater than about 1.0 mg of therapeutic compound/100 grams of vehicle may be useful with 1% w/w hydrogel vehicles in the treatment of skin involvement. Suitable vehicles, in addition to gels, are oil-in-water or water-in-oil emulsions using mineral oils, petrolatum and the like.

The therapeutic compound is optionally administered topically by the use of a transdermal therapeutic system (Barry, *Dermatological Formulations*, (1983) page 181 and literature cited therein). While such topical delivery systems have been designed largely for transdermal administration of low molecular weight drugs, by definition they are capable of percutaneous delivery. They may be readily adapted to administration of the therapeutic compounds of the invention by appropriate selection of the rate-controlling microporous membrane.

Compositions of the invention are presented for administration to humans and animals, preferably in unit dosage forms such as vials, ampules, tablets, caplets, pills, powders, granules, eyedrops, oral or ocular solutions or suspensions, ocular ointments, and oil-in-water emulsions. Topical preparations typically include vehicles suitable for use on the skin or the corneal/conjunctival epithelium, including emollients, emulsifiers, wax, fats, alcohols, and/or oils.

The term "unit dosage form" refers to physically discrete units suitable as unitary doses for human subjects and animals, each unit containing a predetermined quantity of active material calculated to produce a desired pharmaceutical effect in association with the required pharmaceutical diluent, carrier or vehicle.

Slow Release Delivery

Slow or extended-release delivery systems, including any of a number of biopolymers (biological-based systems), systems employing liposomes, and polymeric delivery systems, can be utilized with the compositions described herein to provide a continuous or long term source of therapeutic composition. Such systems can be adapted for not only aerosols (discussed above), but also for other routes of administration including oral, parenteral and topical routes. See, for example, *Remington's*, Chapter 92, pages 1644–1661.

Administration

The composition may be administered by any conventional method for the administration of therapeutics including oral and parenteral (e.g., intravenous (IV), subcutaneous (SQ) and intramuscular (IM)) injection. The treatment may consist of a single dose or a plurality of doses over a period of time. Intravenous administration is preferred when parenteral administration is practiced.

Therapeutic compounds or compositions of the invention can also be delivered or administered topically, by transdermal patches, intraperitoneally (IP), intraarterially, in aerosol form, orally, and in drops among other methods. When the administration is by an infusion, such as IV, the composition can be delivered as a bolus, a short term infusion or a continuous, longer term infusion. Aerosol administration is contemplated not only for inhalation therapy (to the lungs and bronchi), but also for application to the mouth, eye, or skin in appropriate circumstances.

Although humans are a preferred recipient for therapeutic compounds of the invention, veterinary use is also included. For example, it has been reported that the armadillo can be a reservoir for *M. leprae*. Also, some mammals, including livestock such as cattle, sheep and goats, require treatment for mycobacterial infection. Johne's disease, for instance, is an infection of *M. paratuberculosis* in sheep and cattle. Additionally, birds and rodents can harbor mycobacterial infection. Thus, any animal which harbors or which is at risk for harboring mycobacterial infection is a candidate for therapy with the invention.

The condition for treatment includes any mycobacterial infection, active and inactive. Also included is preventative therapy. For instance, if mycobacterial infection is suspected or the recipient is at high risk for development of such an infection, then therapy may be appropriate.

Dosages

The dosage of the specific compound for treatment depends upon many factors that are well known to those skilled in the art. An effective amount of the compound is that which provides either subjective relief of symptoms or an objectively identifiable improvement as noted by the clinician or other qualified observer. The dosing range varies with the compound used, the route of administration and the potency of the particular compound. The compound may be administered by any conventional method for the administration of parenteral agents.

In therapeutic applications, the dosage of compounds used in accordance with the invention vary depending on the class of compound and the condition being treated. The age, weight, clinical condition and medical history of the recipient patient; the severity of the disease being treated; and the experience and judgment of the clinician or practitioner administering the therapy are among the factors affecting the selected dosage. For example, the dosage of a therapeutic compound of the invention ranges from about 10 micrograms per kilogram per day to about 100 milligrams per kg per day, preferably about 100 micrograms to about 1 milligram. The dosage to be administered daily is usually from about 0.01 to 100 mg/kg of body weight, preferably about 0.1 to 10 mg/kg. The dose should be sufficient to ameliorate symptoms or signs of infection without producing unacceptable toxicity to the patient.

Therapeutic compounds of the invention will have low toxicity in mammals because eukaryotes neither utilize nor require cyclopropanated lipids and are probably incapable of oxidatively degrading lipids of this exceptionally long length.

Because the therapeutic compounds result in noncyclopropanation of a portion of the mycolates in the outer coat of the mycobacteria, these bacteria can become more susceptible to host oxidative defenses. Thus, even though bacilli might continue to grow in the presence of low concentrations of these compounds, their cell walls may be altered in such a way as to render them much less able to survive in macrophages. Thus, the actual therapeutic dosage used in humans is often lower than the dosage which would be predicted from in vitro studies.

Because the therapeutic compounds of the invention target a biosynthetic step different from that affected by isoniazid, these compounds could function synergistically with isoniazid or other antibiotics which affect mycolate synthesis. Thus, compounds of the invention can be used in combination with other compounds, such as isoniazid, which are used to treat TB or other infections of mycobacteria. The phrase "in combination" includes simultaneous as well as sequential administration of different compounds. Combination therapy occurs if the recipient has measurable blood levels of the compounds in the combination.

Therapeutic compositions are usually administered at least once daily, typically as an oral dosage or an intravenous infusion. Sometimes the dosage is administered two or more times a day, but a single daily dose is preferred. Preferably, the dosage is repeated daily until either a therapeutic result is achieved or until side effects warrant discontinuation of therapy. Therapy may continue for a month or more, often for 12 to 18 months. A recommended end point of therapy is clearing of the mycobacteria from the afflicted individual or the site, such as the lungs. Evidence of this clearing can be obtained from, for example, an X-ray of the relevant site (such as a chest X-ray to evaluate the lungs); and staining, histological studies, biochemical studies, and culture results of samples taken from the recipient animal. Such samples can be, for instance, fluids (e.g., sputum, bone marrow, cerebrospinal fluid) or tissue (e.g., biopsies of skin, bone, liver, kidney).

Application to Surfaces

Compounds of the invention can be used not only as therapeutics, either alone or in combination or in compositions, but also to promote an antiseptic condition wherever such a condition is appropriate. For example, the compounds can be applied to a surface in need of the antiseptic condition. Examples include any of a number of surfaces, such as those found in hospitals, clinics, medical offices, laboratories, and operating rooms. More specifically the surfaces include operating tables, operating instruments (such as hemostats, forceps and scissors), equipment used by the anesthesiologist (such as laryngoscopes and ventilating equipment "breathing machines", tanks, tubes and devices used to administer oxygen and anesthetic gases), and laboratory equipment, (such as counter tops, centrifuges, flasks, pipets, pumps, etc). Additionally, it may be appropriate to use compounds of the invention as topical antiseptics, such as for the hands of laboratory personnel or operating room personnel.

Application of compounds of the invention for the purpose of promoting an antiseptic environment or condition can be accomplished by any of a number of means, including spraying, pouring, wiping, and immersing the surface in the compound or in a formulation including the compound.

Compounds of the invention used for promoting an antiseptic condition can be formulated by means well known in the art. For example, carriers, surfactants or diluents can be used, such as, for example, those mentioned above in conjunction with pharmaceutical compositions. Additionally, dispersants and wetting agents can be included in the formulation.

The following experimental results are offered by way of example and not by way of limitation.

EXAMPLES

Example 1

This example illustrates the preparation of long-chain alkyl bromides from the commercially available corresponding alcohols. The bromides can be used in subsequent transformations to provide the compounds used in the invention.

1-Nonadecyl bromide

To nonadecanol (1.0 g, 3.5 mmol) was added 1500 μL hydrobromic acid (48% wt/vol). After cooling in ice, concentrated sulfuric acid (400 μL) was added and the reaction was allowed to warm to room temperature. A condenser and drying tube were placed over the reaction and the mixture was slowly heated to 120° C. The solution was kept at reflux for five hours and then cooled. The solidified product was resuspended in a mixture of ethyl acetate (50 mL) and water (10 mL). The aqueous layer was removed and the organic layer was washed with water (2×10 mL), then 5% sodium bicarbonate (10 mL) and then one final time with water. The resulting solution was dried over magnesium sulfate and filtered. The solvent was removed to provide a crude product which was purified by silica chromatography (hexanes:ethyl acetate, 80:20, as eluant) to give the desired 1-nonadecyl bromide (624 mg, 1.79 mmol, 51%). $^1$H NMR (CDCl$_3$, 300 MHz); δ3.40 (t, J=6.9 Hz, 2H), 1.83 (m, 2H), 1.41 (br s, 2H), 1.25 (s, 32H), 0.87 (t, J=6.7 Hz). $^{13}$C NMR (CDCl$_3$.67.93 MHz); δ33.94 32.83, 31.90, 29.65, 29.52, 29.42, 29.33, 28.75, 28.16, 22.66, 14.07. M.S. (EI+); 346 (M+), 267 (M-Br).

Example 2

This example illustrates the synthesis of 4-thiatetracosanoic acid.

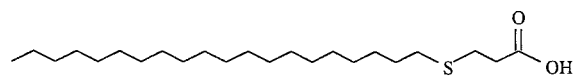

Potassium hydroxide (0.561 g, 10 mmol) was added to absolute ethanol (25 mL) and dissolved while purging with argon. 3-Mercaptopropionic acid (435 μL, 5 mmol) was added followed immediately by 1-bromoeicosane (1.80 g, 5 mmol). This suspension was brought to a reflux under positive argon pressure and kept there for 6–7 hours. After cooling, ethanol was removed under reduced pressure and the residue was partitioned between 1M HCl (50 mL) and ether (50 mL). The ether layer was removed and the aqueous layer was reextracted with 50 mL ether. The combined organic layers were washed once with water and dried over magnesium sulfate, filtered and evaporated to dryness. The residue was purified by silica gel chromatography (methanol:chloroform, 2:98) to give the desired product (393 mg, 1 mmol, 20% yield). $^1$H NMR (CDCl$_3$, 300 MHz); 5 2.77 (t, J=7.4 Hz, 2H), 2.65 (t, J=7.3Hz, 2H), 2.51 (t, J=7.4 Hz, 2H), 1.57 (m, 2H), 1.23 (m, 34H), 0.87 (t, J=6.7 Hz, 3H). $^{13}$NMR (CDCl$_3$, 75.47 MHz); δ177.96, 34.93, 32.54, 32.25, 30.02, 29.93, 29.85, 29.69, 29.56, 29.20, 26.92, 23.01, 14.44. M.S. (EI+, (Me ester)); 400 (20, M+), 313 (100, M-(CH$_2$)$_2$CO$_2$Me).

Example 3

This example illustrates the synthesis of 5-thiatetracosanoic acid.

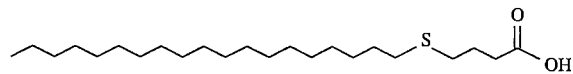

Potassium hydroxide (0.157 g, 2.8 mmol) was added to 7 mL of anhydrous ethanol under argon in a flask equipped with a reflux condenser. After purging with argon for 5 minutes, γ-thiobutyrolactone (121 μL, 1.4 mmol) was added and the solution was stirred for 5 minutes. 1-Nonadecyl bromide (500 mg, 1.4 mmol) was added and the solution was heated to reflux for 2 hours then cooled and partitioned between diethyl ether (25 mL) and 1M HCl (10 mL). The organic layer was separated and the aqueous layer was extracted with an additional 25 mL of ether. The combined organic portions were washed with distilled water (10 mL), dried over magnesium sulfate and evaporated to dryness under reduced pressure. The residue was purified by chromatography as described in Example 2 to give the desired acid (127 mg, 0.33 mmol, 24%). $^1$H NMR (CDCl$_3$ 300 MHz); δ2.55 (t, J=7.2 Hz, 2H), 2.47 (t, J=7.4 Hz, 4H), 1.91 (m, 2H), 1.55 (m, 2H), 1.25–1.32 (br s, 32H), 0.87 (t, J=6.7 Hz). $^{13}$C NMR (CDCl$_3$, 75.47 MHz); δ33.05, 32.25, 31.53, 30.01, 29.86, 29.68, 29.57, 29.24, 24.70, 23.01, 14.43. M.S. (EI+,(Me ester)); 400 (20, M+), 299 (100, M-(CH$_2$)$_3$CO$_2$Me). HR-M.S. m/e 386.3225 (13.2), C$_{23}$H$_{46}$O$_2$S requires 386.3219.

Example 4

This example illustrates the synthesis of 6-thiatetracosanoic acid.

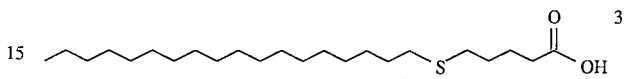

Potassium hydroxide (0.111 g, 2 mmol) was added to anhydrous ethanol (5 mL) under argon in a flask equipped with a reflux condenser. After purging with argon for 5 minutes, octadecyl mercaptan (340 μL, 1.0 mmol) was added and the solution was warmed until the thiol dissolved. 5-Bromovaleric acid (0.181 g, 1 mmol) was added and the solution was heated to reflux under positive argon pressure for 2 hours. After cooling the solution was partitioned between diethyl ether (25 mL) and 1M HCl (10 mL). The organic layer was removed and treated as described in Example 3. The crude product was purified by chromatography on silica gel (methanol:chloroform, 1.5:98.5 as eluant) to provide the desired product (170 mg, 0.44 mmol, 44%). $^1$H NMR (CDCl$_3$, 300 MHz); δ2.50 (t, J=7.4 Hz, 2H), 2.47 (t, J=7.6 Hz, 2H), 2.36 (t, J=7.2 Hz) 1.72 (m, 2H), 1.63 (m, 2H), 1.55 (m, 2H), 1.25–1.32 (br s, 30H), 0.87 (t, J=6.7 Hz, 3H). $^{13}$C NMR (CDCl$_3$, 75.47 MHz); δ33.86, 32.50, 32.24, 31.96, 30.01, 29.86, 29.68, 29.58, 29.27, 24.15, 23.01, 14.43. M.S. (EI+, (Me ester)); 400 (25, M+), 285 (75, M-(CH$_2$)$_4$CO$_2$Me). HR-M.S. m/e 386.3217 (13.2), C$_{23}$H$_{46}$O$_2$S requires 386.3219.

Example 5

This example illustrates the synthesis of 7-thiatetracosanoic acid.

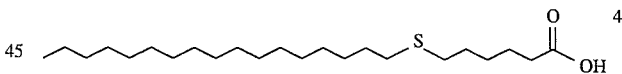

1-Bromoheptadecane (1.0 g, 3.1 mmol) was dissolved in 2 mL of 95% ethanol. Thiourea (238 mg, 3.13 mmol) was added and the solution was heated to reflux. The bromide slowly dissolved over the first hour of heating as the S-alkylisothiouronium salt was formed. After two hours at reflux, sodium hydroxide (543 μL of 6M aqueous, 3.26 mmol) was added under argon to liberate the mercaptan. The mixture was kept at reflux for two more hours as the mercaptan separated out as an oily layer on top of the reaction mixture. After this time, 6-bromocaproic acid (605 mg, 3.1 mmol) was added followed immediately by additional NaOH (1.03 mL of 6M, 6.2 mmol). The resulting mixture was heated at reflux for an additional two hours, then cooled and partitioned between ether (50 mL) and 1M HCl (100 mL). The organic layer was removed and the aqueous layer was extracted two more times with 25 mL portions of ether. The combined ether extracts were washed once with water, dried over magnesium sulfate, and evaporated to dryness under reduced pressure. The residue was purified by chromatography over silica gel (methanol:chloroform, 1:99) to give the desired product (533 mg, 45%). $^1$H NMR (CDCl₃, 300 MHz); δ2.49 (t, J=7.2Hz, 2H), 2.48 (t, J=7.4 Hz, 2H), 2.35 (t, J=7.4 Hz, 2H), 1.58 (m, 6H), 1.43 (m, 2H), 1.23 (br s, 28H), 0.86 (t, J=6.7 Hz, 3H). $^{13}$C NMR (CDCl₃, 75.47 MHz); δ180.12, 34.20, 32.53, 32.24, 30.02, 29.62, 29.29, 28.62, 24.60, 23.02, 14.44. M.S. (EI+, (Me ester)); 400 (30, M+), 285 (90, M-(CH₂)₅CO₂Me).

Example 6

This example illustrates the growth inhibition assays and MIC determinations with *Mycobacterium tuberculosis* H37Ra (FIG. 1ABCD) and with *M. smegmatis* mc²155 (FIG. 2ABCD).

Middlebrook 7H9 media containing ADC (albumin-dextrose complex) and Tween 80 (0.05%) was inoculated from frozen seed and grown for one week in sealed tubes with stir bars. This well-dispersed culture was used to inoculate two 100 mL shaker cultures in the same media to an initial optical density (OD) at 650 nm of 0.1. These cultures were grown to an OD at 650 nm of 0.33 and then diluted 1:200 into two 100 mL cultures. These were grown to an OD at 650 nm of 0.025. When the OD reached 0.025 the two cultures were combined and split into 24 smaller flasks containing 15 mL of the original culture each representing four groups of six flasks each. These contained; (1) 15 μL DMF (dimethylformamide) control, (2) 15 μL 0.1 mg/mL drug, (3) 15 μL 0.4 mg/mL drug, (4) 15 μL 1.6 mg/mL drug, (5) 15 μL 6.4 mg/mL drug, and (6) 15 μL 25.6 mg/mL drug (all drugs in DMF). The stock drug solutions were made up from fourfold serial dilutions of 25.6 mg of each drug in 1 mL DMF. Aliquots (1 mL) of the culture were removed from each flask daily over the course of the experiment and the OD at 650 nm was recorded.

Figure 3:
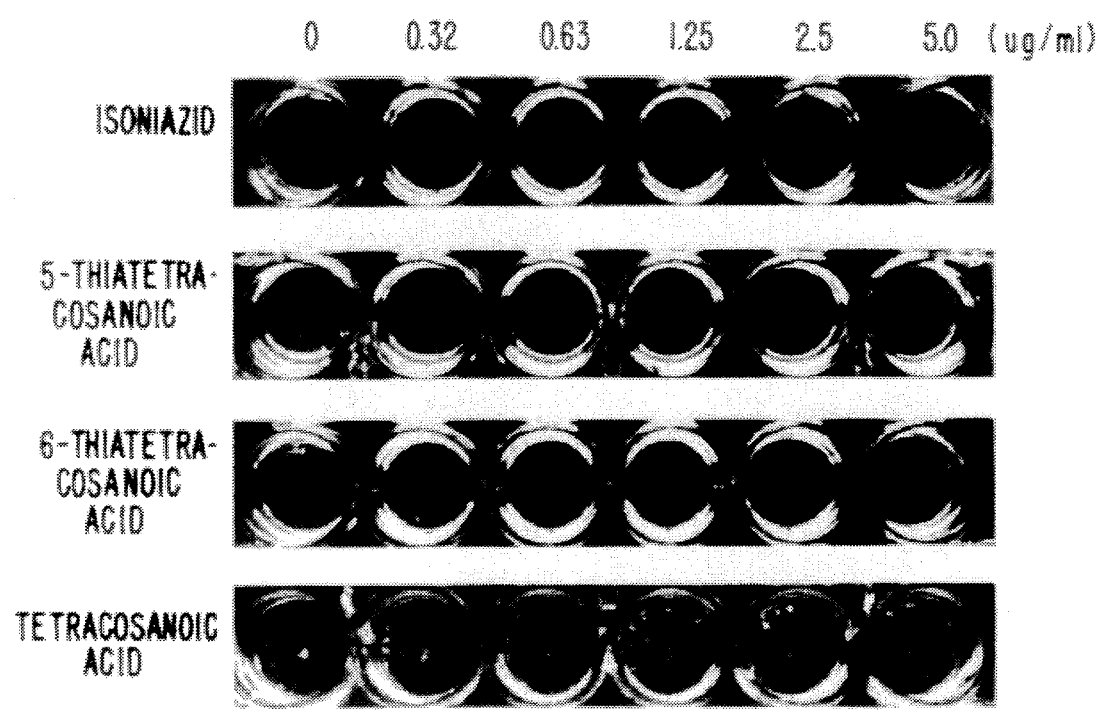
FIG. 3 shows an assay culture of *M. tuberculosis* H37Ra which has been treated with isoniazid, 5-thiatetracosanoic acid, 6-thiatetracosanoic acid and tetracosanoic acid in growth media in the absence of Tween and albumin.

When the experiment using *M. tuberculosis* H37Ra was performed in the absence of Tween, the MIC₅₀ levels were several-fold lower (in the range of 0.63 to 1.0 mg/mL for 4, 6, and 7-thiatetracosanoic acid) than when Tween was present. FIG. 3 shows a comparison of *M. tuberculosis* H37Ra in GAS media which has been treated with isoniazid, 5-thiatetracosanoic acid, 6-thiatetracosanoic acid and tetracosanoic acid. GAS media is a synthetic media containing H₂O (990 mL, pH 6.6), Bacto Casitone (a milk digest, 0.3 g/L), ferric ammonium citrate (0.05 g/L), K₂HPO₄ (4.0 g/L), citric acid (2.0 g/L), L-alanine (1.0 g/L), MgCl₂ hexahydrate (1.2 g/L), K₂SO₄ (0.6 g/L), NH₄Cl (2.0 g/L), 10.0M NaOH (1.8 mL/L), and glycerol (10.0 mL/L). In this experiment, GAS media containing the indicated levels of the antimycobacterial agents was inoculated with *M. tuberculosis* H37Ra and the cultures were grown for 10–14 days. Visual inspection provides an indication of the MIC₅₀ values for the four agents. As FIG. 3 indicates, tetracosanoic acid has no effect of the mycobacteria and the MIC₅ values for 5-thiatetracosanoic acid, 6-thiatetracosanoic acid and isoniazid are ~2.5 μg/mL, 0.63–1.25 μg/mL, and less than 0.32 μg/mL, respectively.

The data from the experiment using *M. smegmatis* (FIG. 2ABCD) show no significant effect of the compounds on cell growth. This finding supports the theory that the immediate target of these compounds is an enzymatic pathway unique to pathogenic mycobacteria (such as *M. tuberculosis*), but absent from saprophytic strains (such as *M. smegmatis*).

The foregoing is offered primarily for purposes of illustration. It will be readily apparent to those skilled in the art that the structures, methods, composition components, syntheses and use conditions, and other parameters of the system described herein may be further modified or substituted in various ways without departing from the spirit and scope of the invention. Thus, the invention is not limited by the description and examples, but rather by the appended claims and their equivalents.

What is claimed is:

1. A pharmaceutical composition comprising, in unit dosage form, a compound of formula I,

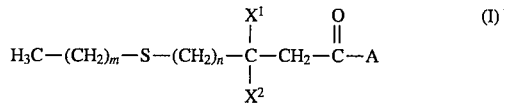

wherein n is an integer of from 0 to 3;

m is an integer of from 12 to 23, with the proviso that n+m is from 15 to 23;

A is selected from the group consisting of —O³¹, its pharmaceutically acceptable salts, —OH, and —OR;

wherein

R is an alkyl group having from 1 to 10 carbons; and

X¹ and X² are each independently selected from the group consisting of H and F; and a sterile pharmaceutically acceptable carrier.

2. A composition of claim 1 wherein n is an integer of from 0 to 3, m is an integer of from 15 to 20 with the proviso that n+m is from 18 to 20.

3. A composition of claim 1 wherein n is an integer of from 0 to 3, m is an integer of from 15 to 20 with the proviso that n+m is from 18 to 20, R is an alkyl group having from 1 to 4 carbons, and X¹ and X² are both H.

4. A composition of claim 3 wherein n+m is 19.

5. A composition of claim 1 wherein n+m is 19, X¹ and X² are both H, and A is selected from the group consisting of —O⁻, its pharmaceutically acceptable salts and —OH.

* * * * *